United States Patent [19]

Maeda et al.

[11] Patent Number: 4,479,609

[45] Date of Patent: Oct. 30, 1984

[54] LIQUID SPRAYER

[75] Inventors: Masatoshi Maeda; Tomohiro Kami; Toshio Kusunoki; Yukio Yamamura, all of Shiga, Japan

[73] Assignee: Matsushita Electric Works, Ltd., Osaka, Japan

[21] Appl. No.: 416,607

[22] Filed: Sep. 10, 1982

[30] Foreign Application Priority Data

Oct. 9, 1981 [JP] Japan ................................ 56-161169

[51] Int. Cl.³ .............................................. B05B 1/26
[52] U.S. Cl. ........................... 239/102; 261/DIG. 48; 261/DIG. 65; 261/81
[58] Field of Search ....................... 239/4, 102, 44, 49; 261/1, 81, 99, DIG. 48, DIG. 65

[56] References Cited

U.S. PATENT DOCUMENTS

| 1,718,182 | 6/1929 | Rose et al. | 261/99 |
| 2,786,714 | 3/1957 | Saleny | 261/99 |
| 3,103,310 | 9/1963 | Lang . | |
| 4,301,093 | 11/1981 | Eck | 239/102 |
| 4,334,531 | 6/1982 | Reichl et al. | 239/102 |

Primary Examiner—John J. Love
Assistant Examiner—Jon M. Rastello
Attorney, Agent, or Firm—Stevens, Davis, Miller & Mosher

[57] ABSTRACT

A liquid sprayer comprises an ultrasonic vibrator, a liquid supply chamber, and a liquid absorber for absorbing liquid from the liquid supply chamber and feeding it to the ultrasonic vibrator. The liquid absorber abuts against the lateral side of the utmost end of the ultrasonic vibrator in the vibration direction thereof and projects at the front surface thereof ahead of the utmost end of the ultrasonic vibrator.

3 Claims, 16 Drawing Figures

LIQUID SPRAYER

BACKGROUND OF THE INVENTION

This invention relates to a liquid sprayer which sprays water as fine particles by means of vibrations of an ultrasonic vibrator, and more particularly to such a sprayer which can be used to inject fine water particles into the nasal cavity or mouth cavity of a human body, whereby a mucous membrane is wetted to relieve dryness and allay inflammation of the membrane.

Figure 1:
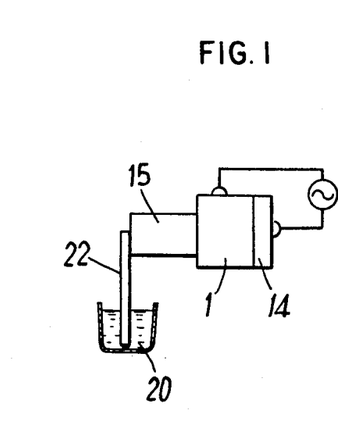
FIG. 1 is a schematic view exemplary of a conventional liquid sprayer.
Figure 2:
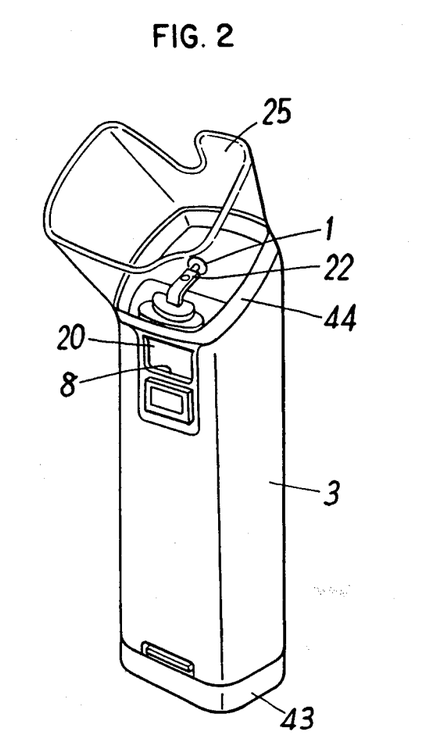
FIG. 2 is a perspective external view of a first embodiment of the liquid sprayer of the invention.

A problem with an apparatus for spraying water as fine particles by use of ultrasonic vibrations is that it is difficult to supply water onto the spraying surface. Conventionally, a water absorber 22, as shown in FIG. 1, is immersed at its lower end into a water-supply tank 20 to absorb water. The absorber abuts at its upper end against a vibrating surface at the utmost end of a metallic horn 15 of an ultrasonic vibrator 1 incorporating an electrostriction element. This arrangement, which equalizes an amount of water supplied to an amount of water sprayed, supplies the water in a stable fashion, but since the water absorber 22 abuts against a portion of the metallic horn of ultrasonic vibrator 1 which has the largest amplitude magnitude, a substantial vibration load caused by the abutment occurs which may make spraying impossible. Also, when the water absorber 22 is small-sized to reduce the contact load with the ultrasonic vibrator 1, the amount of water sprayed decreases.

SUMMARY OF THE INVENTION

In the light of the above problem, this invention has been designed. An object of the invention is to provide a liquid sprayer which imposes less vibration load on its ultrasonic vibrator while achieving a large amount of spray using less electric power, thereby enabling efficient spraying.

Another object of the invention is to provide a liquid sprayer which provides a support at a casing carrying an ultrasonic vibrator, the support supporting a water absorber at the utmost end thereof to thereby reliably position the water absorber with respect to the vibrating surface at the utmost end of the ultrasonic vibrator.

Still another object of the invention is to provide a liquid sprayer which facilitates initial vibration of the ultrasonic vibrator and supplies water smoothly to the ultrasonic vibrator from the water absorber.

Still another object of the invention is to provide a simply constructed water absorber which can withstand long use.

Still another object of the invention is the provision of a return system for a liquid sprayer which allows water drops attached to the edge of a spray jet bore to be returned into a water-supply tank to prevent the water from spilling onto the outer surface of the casing.

These and other objects and advantages of the invention will become more apparent from the following detailed description which is provided in connection with the accompanying drawings.

BRIEF DESCRIPTION OF THE DRAWINGS

FIGS. 5 (a), (b) and (c) are front, upper and sectional views of the water absorber respectively used in the FIG. 2 embodiment;

FIGS. 10 (a) and (b) are views explanatory of the function of the liquid sprayer of the invention;

DETAILED DESCRIPTION OF THE INVENTION

A first embodiment of the liquid sprayer of the invention will be described in accordance with FIGS. 2 through 11, in which reference numeral 3 denotes a molded synthetic resin casing. The casing 3 is partitioned at the upper portion substantially vertically by a partition 6 which has a substantially round opening for mounting an ultrasonic vibrator 1. An oscillation circuit 9 for operating the ultrasonic vibrator 1 and a power supply switch 10 therefor are mounted on a printed wiring substrate 41 housed in the casing 1 and directly below the partition 6. A power supply unit 11 is provided below the substrate 41 and is of the dual power-supply system type which employs dry cells 12, or uses a domestic A.C. power source through an external A.C. source adapter which is connected to a jack box 13.

Figure 3:
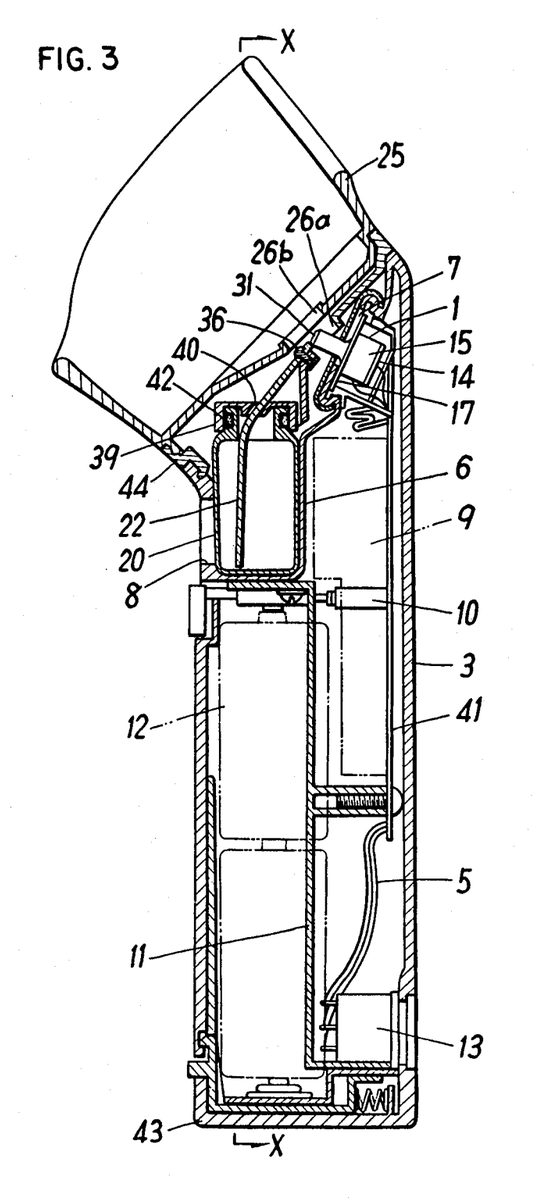
FIG. 3 is a longitudinally sectional view of the FIG. 2 embodiment.
Figure 4:
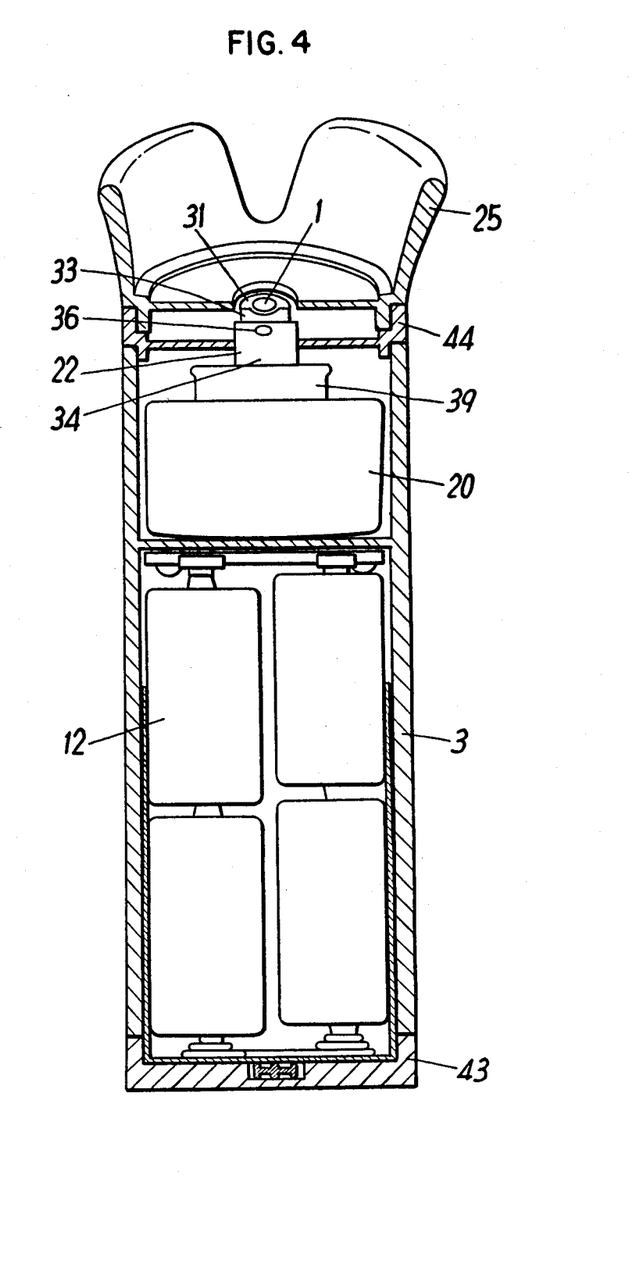
FIG. 4 is a sectional view taken on the line X—X in FIG. 3.
Figure 5A:
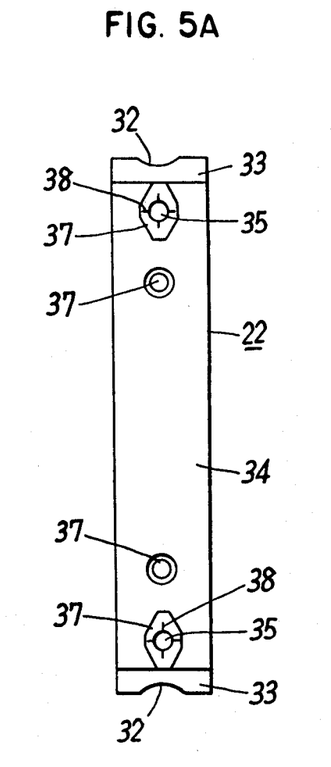
Figure 5B:
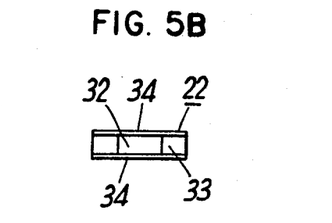
Figure 5C:
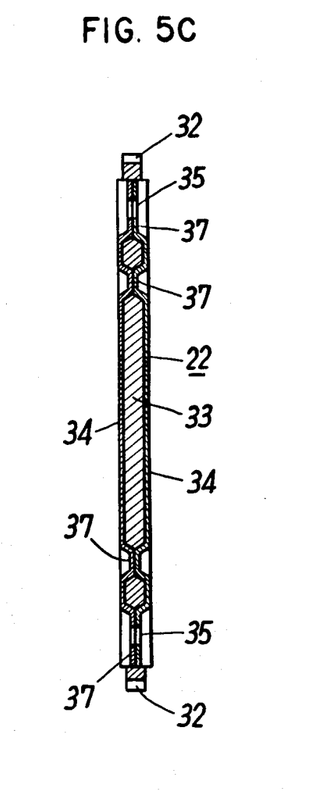
Figures 6, 7, 8:
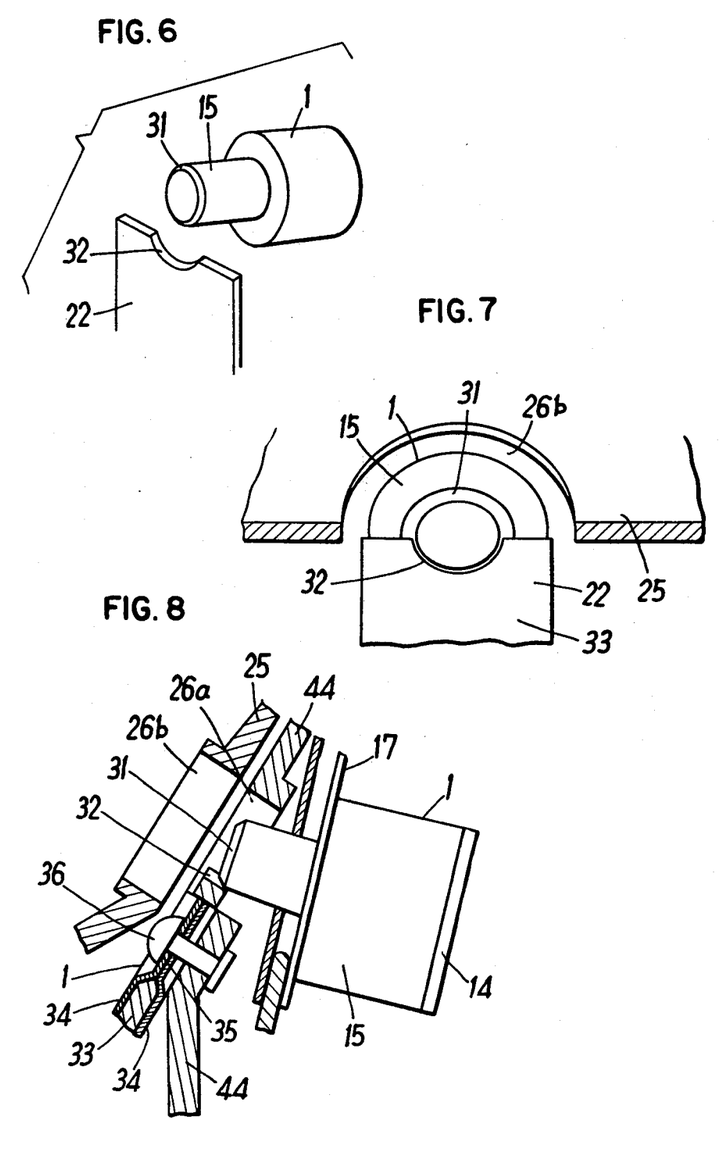
FIG. 6 is a perspective exploded view of the ultrasonic vibrator and water absorber which are partially cutaway.
FIG. 7 is a perspective view of the water absorber in a condition of abutting against the ultrasonic vibrator.
FIG. 8 is a sectional view showing the same condition as in FIG. 7.

The ultrasonic vibrator 1 comprises an electrostriction element 14 for generating vibrations and a metallic horn 15 for enlarging the vibrations. The electrostriction element 14 has one electrode at the center of its rear surface and the other electrode connected electrically with the metallic horn 15 by means of a conductive adhesive. An annular flange 17 is provided at the outer periphery of metallic horn 15 and supports the ultrasonic vibrator 1 at the lower surface of the mounting opening 7, a tapered chamfered portion 31 being formed at the outer edge of the utmost end of metallic horn 15 at the ultrasonic vibrator.

Reference numeral 20 denotes a water-supply tank set detachably onto the partition 6 and formed of a transparent or semitransparent material so that the amount of water in the tank 20 can be seen. A tank cap 39 is mounted on the water-supply tank 20 in a water-tight manner through an O-ring 42 and has a slanted guide bore 40, which holds a water absorber 22 which gently bends through the bore 40. A gentle bending of water absorber 22 is preferred as an extreme bend in the absorber can result in a reduction in absorption of water.

The casing 3 is provided with a window 8 through which an amount of water in the water-supply tank 20 can be visually checked. The water absorber 22 is formed of a core 33 of a bandshaped felt, such as a nonwoven fabric made from acrylic resin, the core 33 being sandwiched at both sides with protector plates 34 of molded synthetic resin such as polypropylene, the protector plates 34 being welded partially with each other to be integral, thus forming a lengthwise symmetrical construction. A mounting bore 35 is provided at the respective welded portion of protector plates 34 and is provided at its periphery with a plurality of slits 38. The core 33 projects at both lengthwise ends thereof somewhat from both lengthwise ends of protector plate 34 and provides cutouts 32 each of a circular arc slightly larger in curvature than the utmost end portion of metallic horn 15. The casing 3 has at the bottom a detachable bottom lid 43 and at the upper portion an accent ring 44 and transparent detachable mask 25. Spraying openings 26a, 26b opposite to the vibrator mounting opening 7 are provided at the accent ring 44 and mask 25 respectively and a hook button 36 projects in the vicinity of spraying opening 26a at the accent ring 44 to form a suppport.

Figure 11:
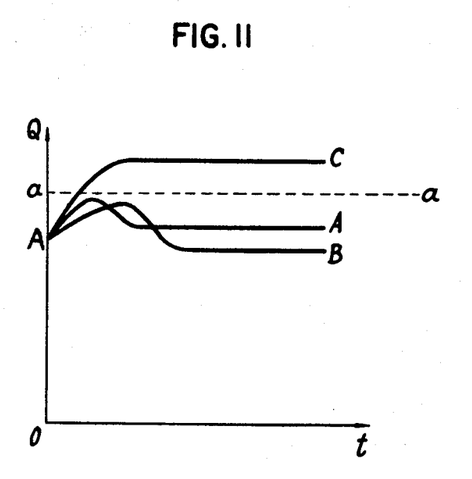
FIG. 11 is a graph showing the relationship between the lapse of time from the start of vibration of the ultrasonic vibrator and the amount of water attached thereto.

The water absorber 22 is inserted through the guide bore 40 and immersed at one end into the water in the watersupply tank 20 and fitted at the other end detachably into the hook button 36, thereby being properly positioned allowing the cutout 32 of a circular arc to abut slantwise against the chamfered portion 31 at the utmost end portion of ultrasonic vibrator 1, in which the front surface of core 33 projects frontwards from the utmost end of ultrasonic vibrator 1. Thus, the mounting bores 35 for fixing the water absorber 22 are provided at the portion 37 of protector plates 34 where they are welded to each other, whereby a strong fitting force of hook button 36 makes it difficult for the water absorber 22 to escape and the provision of slits 38 facilitates the detachable mounting of water absorber 22 and avoids deterioration of the fitting force caused by expansion of mounting bore 35 even with repeated mounting or dismounting of the water absorber 22, thereby positioning the absorber 22 with accuracy. The water absorber 22, which abuts slantwise against the chamfered portion 31 provided at the metallic horn 15 of ultrasonic vibrator 1, is not shifted longitudinally (axially) with respect to the ultrasonic vibrator 1 and its abutting position is stabilized to provide a uniform amount of spray. Also, the provision of the chamfered portion reduces the amount of electric power necessary for the initial spraying and the abutting of the cutout 32 of circular arc at the water absorber 22 against the ultrasonic vibrator 1 keeps the water absorber 22 from projecting onto the vibrating surface to thereby increase the amount of spray in comparison with the consumed electric power and restrain the water absorber 22 from moving sideways.

Upon turning on the power supply switch 10, high-frequency voltage generated by the oscillation circuit 9 and of a frequency about equal to the mechanical resonance frequency of metallic horn 15 is applied on one side directly to the electrostriction element 14 via lead wires 5 and on the other side to the same via the metallic horn 15 and conductive adhesive. The ultrasonic vibrations generated by the electrostriction element 14 are integral with vibrations of metallic horn 15 so that the spraying surface at the utmost end of metallic horn 15 vibrates in greater magnitude by the amplitude enlarging function of metallic horn 15, while the core 33 of water absorber 22 absorbs water by capillary action from the water-supply tank 20 so as to feed the water in a thin film state onto the vibrating surface at the utmost end of metallic horn 15 as shown in FIG. 10(*a*). The vibrations from the vibrating surface cause wave motion of the water and the wave crests are broken to produce a frontward spray. The water absorber 22, when positioned behind the vibrating surface at the utmost end of ultrasonic vibrator 1, makes it difficult to properly feed water onto the vibrating surface, but the present invention has the water absorber projected ahead of the utmost end of ultrasonic vibrator 1, thereby enabling the water to be fed smoothly thereto. Also, since the radial vibration of ultrasonic vibrator 1 is 1/400 or less in comparison with longitudinal vibration, the water absorber 22 of the invention, which abuts against the lateral side of ultrasonic vibrator 1, has considerably less influence on the vibrations.

In fact, the present invention, in comparison with the case where the water absorber 22 contacts with the vibrator 15 as shown in FIG. 1, can reduce the electric power necessary for the spraying by a factor of about one half and also enables the water absorber 22 to be made sufficiently larger in thickness to reach the metallic horn 15 so as to absorb a sufficient amount of water. Further, the water absorber 22, when made larger in width than the metallic horn 15 in radius, can avoid its escape from the horn 15 even when shifted sidewise relative thereto.

The advantages of the invention will be seen from FIG. 11, in which the ordinate axis represents an amount of water Q attached to the vibrating surface at the utmost end of metallic horn 15 and the abscissa axis represents the lapse of the time from a start of vibration of the metallic horn 15. The dotted line a-a shows a limit of the amount of water attached to the vibrating surface of metallic horn 15 so that, when the amount of water exceeding the limit line a-a is attached to the vibrating surface of metallic horn 15, a spray is not produced even with horn 15 vibration. Now, when an amount A of water is attached to the metallic horn 15 just before the start of vibration, the amount of water attached to the metallic horn 15, when the latter vibrates, will change in amount for three conditions as shown by the solid lines A-C, A-A and A-B due to different resistances of water absorber 22 against a water current. In other words, the solid line A-C shows the case where the aforesaid resistance is small and the amount of water begins to increase simultaneously with the initial vibration of metallic horn 15 and soon exceeds the limit of the dotted line a-a. In this case, the metallic horn 15 continuously vibrates but only produces little spray or none at all. The solid line A-B shows a case where the aforesaid resistance is larger than that in the former case and the amount of attached water increases simultaneously with the start of vibrations of metallic horn 15, but decreases after the lapse of time and then is kept in a stable condition. In this case, the change of attached water does not exceed the dotted line a-a of the limit of amount of the attached water, whereby the spray is produced and the water absorber 22 is functioning in normal use. In this case, however, there is a problem in that the amount of spray is less than it could be because the resistance of water absorber 22 against the water current is larger. The solid line A-A shows a case where the water absorber 22 of the invention is used. In this case, the core 33 of low resistance against water current is sandwiched at both sides with the protector plates 34 and has the welded portions 37 to thereby partially increase the resistance value against the water current. With the invention the amount of attached water increase at the initial stage, but does not exceed the limit a-a of the amount of attached water to smoothly produce the spray and the amount of spray is increased even in the stable condition as compared with the case shown by the solid line A-B.

When the water-supply tank 20 is emptied of water, the water absorber 22 is removed from the hook button 36 and the water-supply tank 20 together with the water absorber 22 is taken out of the casing 3 and filled with water, at which time the core 33, which is sandwiched by the protector plates 34, is not soiled with the user's hand so that the sprayer remains sanitary and capable of providing a clean spray.

Figure 9:
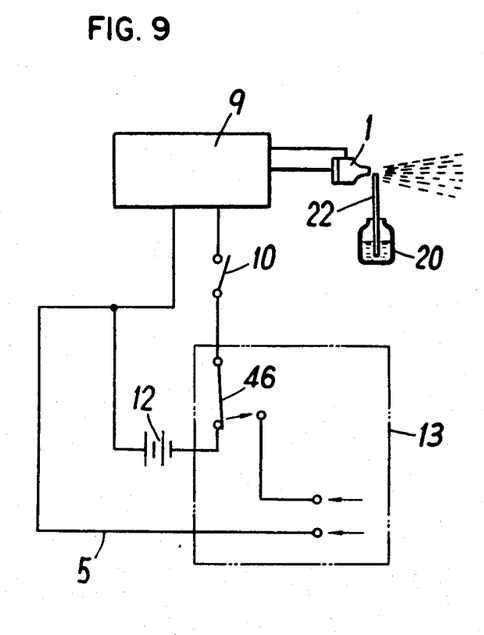
FIG. 9 is a circuit diagram of the liquid sprayer of the invention.
Figure 10A:
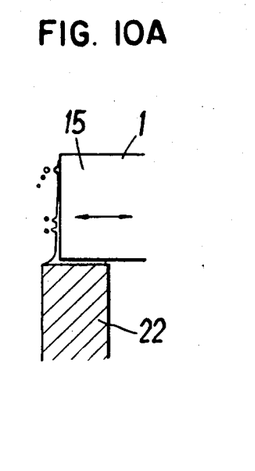
Figure 10B:
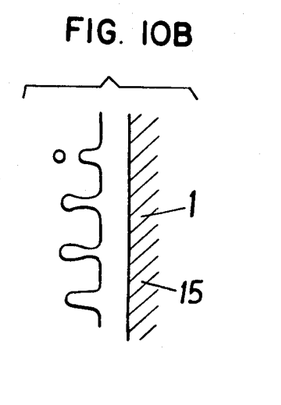

FIG. 9 is a circuit diagram of the liquid sprayer of the invention. Jack box 13 is connectable with an adapter for an external A.C. power supply, whereby a switch 46 is changed over to open the dry cell circuit, thereby enabling the use of a domestic A.C. power source.

As seen from the above, the liquid sprayer of the invention is so constructed that the water absorber, which absorbs water to feed it to the ultrasonic vibrator, abuts against the lateral side of the fore end portion thereof and the upper end of water absorber 22 is positioned ahead of the utmost end of the ultrasonic vibrator, whereby the ultrasonic vibrator contacts with the water absorber at a small contact area to reduce the vibration load on the ultrasonic vibrator and also the vibrating surface is supplied smoothly and reliably with water, thus being advantageous in that a large amount of sprayed water is obtainable with less electric power.

Figure 12:
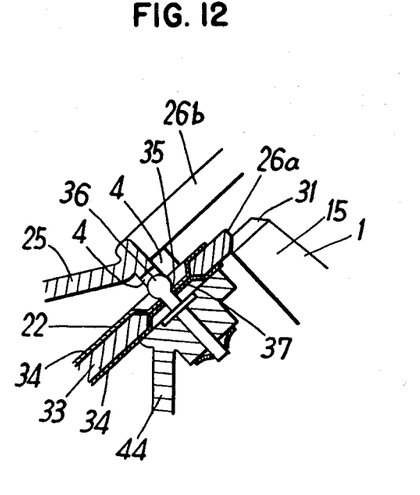
FIG. 12 is a partially enlarged view showing a relation between the ultrasonic vibrator and the water absorber in a second embodiment of the invention; and, FIG. 13 is a perspective partially enlarged sectional view explanatory of the relationship between a mask and the water absorber in the second embodiment of the invention.
Figure 13:
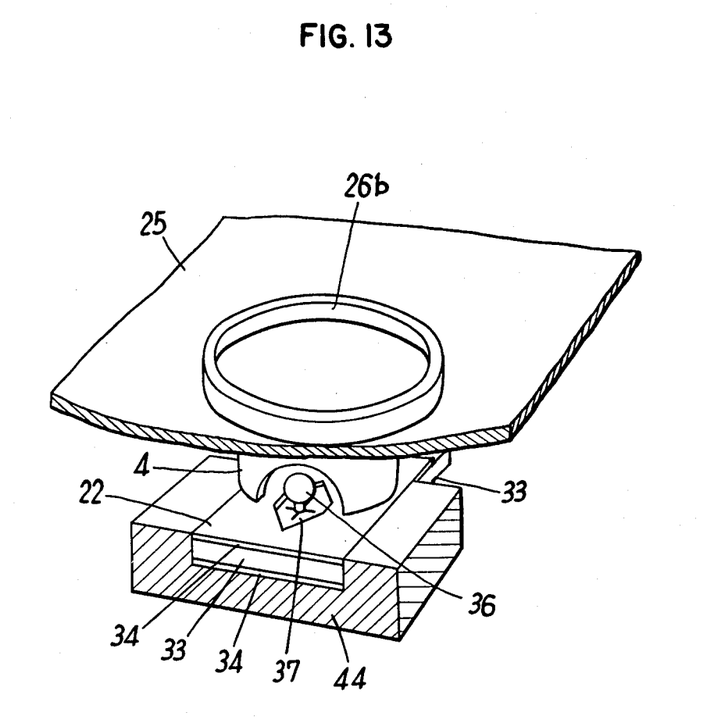

Next, referring to FIGS. 12 and 13, a second embodiment of the invention will be described. In the second embodiment, a spray jet bore 26b is provided at its lower edge with a water cutting rib 4 projecting backwardly in circular arc so that the rib 4, when mounting the mask 25, abuts at the utmost end against the surface of water absorber 22. Hence, even when the water absorber 22 is repeatedly mounted or dismounted which loosens the mounting bore 35 and hook button 36 due to deterioration of their fitting strengths, the water-cutting rib 4 holds down the water absorber 22 so it does not rise or shift, thereby avoiding a poor spraying condition. Furthermore, when in spraying condition, a part of sprayed water is attached to the edge of spray jet bore 26b, but condenses in water drops and flows along the watercutting rib 4 and onto the water absorber 22 and then downwardly along the surface of protector plates 34, and thereafter is collected in the water-supply tank 20 through the guide bore 40, whereby there is no fear that the water spills out from the window 8 or the like.

Although various embodiments of the invention have been shown and described they are merely exemplary as various modifications can be made without departing from the spirit or scope of the invention.

What is claimed is:

1. A liquid sprayer comprising a casing having a support portion, an ultrasonic vibrator carried by said casing, a liquid supply chamber and a liquid absorber for absorbing liquid from said liquid supply chamber and feeding it to said ultrasonic vibrator, said liquid absorber being formed of a core material having liquid absorption properties, said core material being covered lengthwise with extending protector plates, said protector plates being secured to each other partially through said core material to increase the value of resistance against liquid current flowing through said liquid absorber, said core abutting against the lateral side of the utmost end of said ultrasonic vibrator in the vibration direction thereof and projecting outwardly of the utmost end of said ultrasonic vibrator, said liquid absorber being supported at the partially fixed portion of said protector plates by said support portion.

2. A liquid sprayer according to claim 1, wherein said core material is of a thin plate and is sandwiched at both sides thereof with said protector plates each being of a thin plate-like shape in such a manner that all of the lateral and longitudinal sides of the core material are enclosed.

3. A liquid sprayer according to claim 1, wherein said liquid absorber is formed symmetrically in the longitudinal direction thereof and has two fixed portions of said protector plates at longitudinally symmetrical positions thereof so that the liquid absorber may be turned end-for-end.

* * * * *